United States Patent
Zachmann et al.

(10) Patent No.: US 8,037,752 B2
(45) Date of Patent: Oct. 18, 2011

(54) APPARATUS FOR MEASURING THE FILLING LEVEL OF A LIQUID IN A CONTAINER

(75) Inventors: Wilfried Zachmann, Rëmchingen (DE); Thomas Hartmann, Neubulach (DE)

(73) Assignee: Robert Seuffer GmbH & Co. KG, Calw (DE)

( * ) Notice: Subject to any disclaimer, the term of this patent is extended or adjusted under 35 U.S.C. 154(b) by 468 days.

(21) Appl. No.: 12/226,179

(22) PCT Filed: Apr. 12, 2007

(86) PCT No.: PCT/EP2007/003267
§ 371 (c)(1),
(2), (4) Date: Oct. 8, 2008

(87) PCT Pub. No.: WO2007/118677
PCT Pub. Date: Oct. 25, 2007

(65) Prior Publication Data
US 2009/0038394 A1      Feb. 12, 2009

(30) Foreign Application Priority Data

Apr. 12, 2006 (DE) .......................... 10 2006 017 284
Apr. 5, 2007 (DE) .......................... 10 2007 016 539

(51) Int. Cl.
*G01F 23/296* (2006.01)
(52) U.S. Cl. ..................................... 73/290 V

(58) Field of Classification Search ................. 73/290 V
See application file for complete search history.

(56) References Cited

U.S. PATENT DOCUMENTS 5,697,941 A * 12/1997 Christy .................. 606/144

FOREIGN PATENT DOCUMENTS

| DE | 19627199 A1 | * | 1/1997 |
| JP | 2004101486 A | * | 4/2004 |
| JP | 2005106548 A | * | 4/2005 |
| JP | 2005127919 A | * | 5/2005 |
| JP | 2005140640 A | * | 6/2005 |
| JP | 2005201871 A | * | 7/2005 |
| JP | 2006047056 A | * | 2/2006 |

* cited by examiner

*Primary Examiner* — Hezron E Williams
*Assistant Examiner* — Paul West
(74) *Attorney, Agent, or Firm* — Ware, Fressola, Van Der Sluys & Adolphson LLP

(57) ABSTRACT

Apparatus for measuring the filling level of a liquid in a container comprising a transmitting device 1 which emits ultrasound transmission pulses, a receiving device 2 which receives the echo signals reflected at the surface of the liquid and an evaluation device 8 which evaluates the transit times of the ultrasound transmission pulses and echo signals, wherein arranged at a given spacing relative to the transmitting/receiving device 1, 2 is a reflector 3 which reflects the ultrasound transmission pulses in the direction of the surface of the liquid and also reflects the echo signals coming from the surface of the liquid in the direction of the receiving device 2.

23 Claims, 5 Drawing Sheets

APPARATUS FOR MEASURING THE FILLING LEVEL OF A LIQUID IN A CONTAINER

BACKGROUND OF THE INVENTION

1. Technical Field of the Invention

The invention concerns an apparatus for measuring the filling level of a liquid in a container.

2. Description of the Background Art

An apparatus of that kind is known from US No 2005/0284217 A1. The known apparatus comprises, in a container in which the liquid is to be arranged, a transmitting/receiving device which emits ultrasound transmission pulses and receives echo pulses which are reflected at the surface of the liquid and which are caused by the ultrasound transmission pulses. In an evaluation device, the transit times of the ultrasound transmission pulses and the echo signals in the liquid are evaluated to determine the filling level. In the known apparatus, the transmitting/receiving device is arranged in a housing comprising two tubular housing portions which are angled relative to each other at a right angle, at an end of the housing portion extending substantially parallel to the bottom of the container, and a reflector is arranged in the angled region. The reflector deflects the ultrasound transmission pulses emitted by the transmitting/receiving device at an angle through 900 in a direction towards the surface of the liquid. The echo signals reflected there are reflected back by the reflector to the transmitting/receiving device. In the known apparatus the reflector is held in position in the angled housing region by means of an additional holding device.

SUMMARY OF THE INVENTION

The object of the invention is to provide an apparatus of the kind set forth in the opening part of this specification, which permits a simple installation of the reflector and the transmitting/receiving device in the interior of the housing.

In accordance with the invention that object is attained by the features of claim 1.

Advantageous developments of the invention are recited in the dependent claims.

The invention provides that disposed at a given spacing relative to the transmitting and receiving device which is preferably in the form of a structural unit is a reflector which reflects the ultrasound transmission pulses in the direction towards the surface of the liquid and passes the echo signals coming back therefrom back in the direction towards the receiving device. In that case, the ultrasound transmission pulses are emitted substantially parallel to the bottom of the container, in particular horizontally. The ultrasound transmission pulses are deflected by the receiver towards the surface of the liquid in such a way that they impinge substantially at a right angle onto the surface of the liquid. Horizontally emitted ultrasound transmission pulses are thus deflected in a vertical direction. The reflector is preferably so arranged that the ultrasound transmission pulses and the echo signals are deflected at a right angle. The apparatus according to the invention makes it possible to still satisfactorily detect even low filling levels.

In a preferred arrangement, the transmitting/receiving device and the reflector are disposed in the immediate proximity of the container bottom. In that arrangement the ultrasound transmission pulses are emitted substantially parallel to the container bottom to the reflector. The reflector is in the form of a plane, for example a surface which comprises metal or plastic material and at which the ultrasound transmission pulses are reflected. Preferably that surface or the reflector is at an angle of for example 45° relative to the container bottom.

In a preferred embodiment, a reference surface which reflects the ultrasound transmission pulses and which can also be formed from metal or plastic material is arranged in the proximity of the container bottom at a given spacing relative to the transmitting and receiving device. Preferably the reference surface reflects the ultrasound transmission pulses back to the transmitting and receiving device, in a direction in opposite relationship to the direction of incidence. The transmitting/receiving device, the reflector and the reference surface can be arranged in a tube which extends substantially parallel to the container bottom and which can comprise metal or plastic material.

The transmitting/receiving device is arranged at the one end of the tube, which is opened around the axis of the tube, and the reflector and the reference surface are arranged at the other end of the tube. An opening is provided in the peripheral portion of the tube, in the region of the reference surface. A second tube can be connected to that opening. The second tube, like the first tube extending parallel to the container bottom, serves as an ultrasound guide means. The two tubes are preferably integrally connected together at a right angle to form an angled tube.

Evaluation of the transit times of the ultrasound transmission pulses from the transmitting device to the reference surface and the corresponding echo signals which are reflected back makes it possible to detect physical properties of the liquid, in particular differences in density, temperature fluctuations, levels of concentration of components contained therein and the like, which influence the speed of propagation of the ultrasonic waves in the liquid. Upon evaluation of the ultrasound transmission pulses deflected at the reflector and the associated echo signals, the shifts or changes in the speed of propagation of the ultrasonic waves, resulting from changes in the physical properties of the liquid, are taken into consideration.

Preferably the reference surface is arranged in the immediate proximity of the reflector and can be formed in one piece with the reflector.

In a preferred embodiment the housing comprises two half-shell portions which are fixedly connected together at longitudinally extending connecting surfaces. The connection can be made by welding, in particular pulse welding, or by latching elements which engage into each other and which extend along the connecting surfaces, for example in the form of sealing lips. The half-shell portions are also in the form of angled half-shell portions, for the purposes of adaptation to the housing which substantially comprises two angled tubes. The angle between the tubular housing portions is for example 90°, as in the known apparatus. It is also possible to involve other suitable angles. The invention however provides a continuous self-supporting angular housing, by means of the two half-shell portions. Additional, externally disposed holding elements for the reflector are not required. For that purpose, formed at the inside surfaces of the half-shell portions are suitable openings in which the reflector can be pre-mounted for example by insertion or by being fitted thereinto, in the angled region of the housing, before the two half-shell portions are assembled. In addition, for the transmitting/receiving device which is in the form of providing for electrical transformation, arranged at the corresponding end of the tube portion arranged substantially parallel to the housing bottom, at the inside surfaces of the two half-shell portions, are suitable openings for holding the transmitting/receiving device, in particular for holding it in positively locking relationship.

The component parts of the measuring apparatus can thus be easily fitted into each other, in which case the transmitting/receiving device and the reflector are firstly pre-assembled in the appropriate positions in the interior of the housing and, when the two half-shell portions are fitted together and connected together, they are held fixedly in the desired position preferably in positively locking relationship in the associated openings in the interior of the housing.

Preferably two hollow spaces extending in mutually parallel relationship can be formed in the housing. The two hollow spaces are sealed off relative to each other, in which case central connecting surfaces at which the two housing shell portions are connected together ensure sealing separation of the two hollow spaces. The one hollow space serves preferably for conducting the ultrasonic waves and the other hollow space serves to guide electric lines which can be connected together to afford a cable and connect the transmitting/receiving device to a power supply and the evaluation device. Other electrical or electronic components for example in the evaluation device can also be arranged in that other hollow space.

BRIEF DESCRIPTION OF THE DRAWINGS

The invention is described in greater detail hereinafter with reference to the Figures in which.

DETAILED DESCRIPTION OF THE INVENTION

Figure 1:
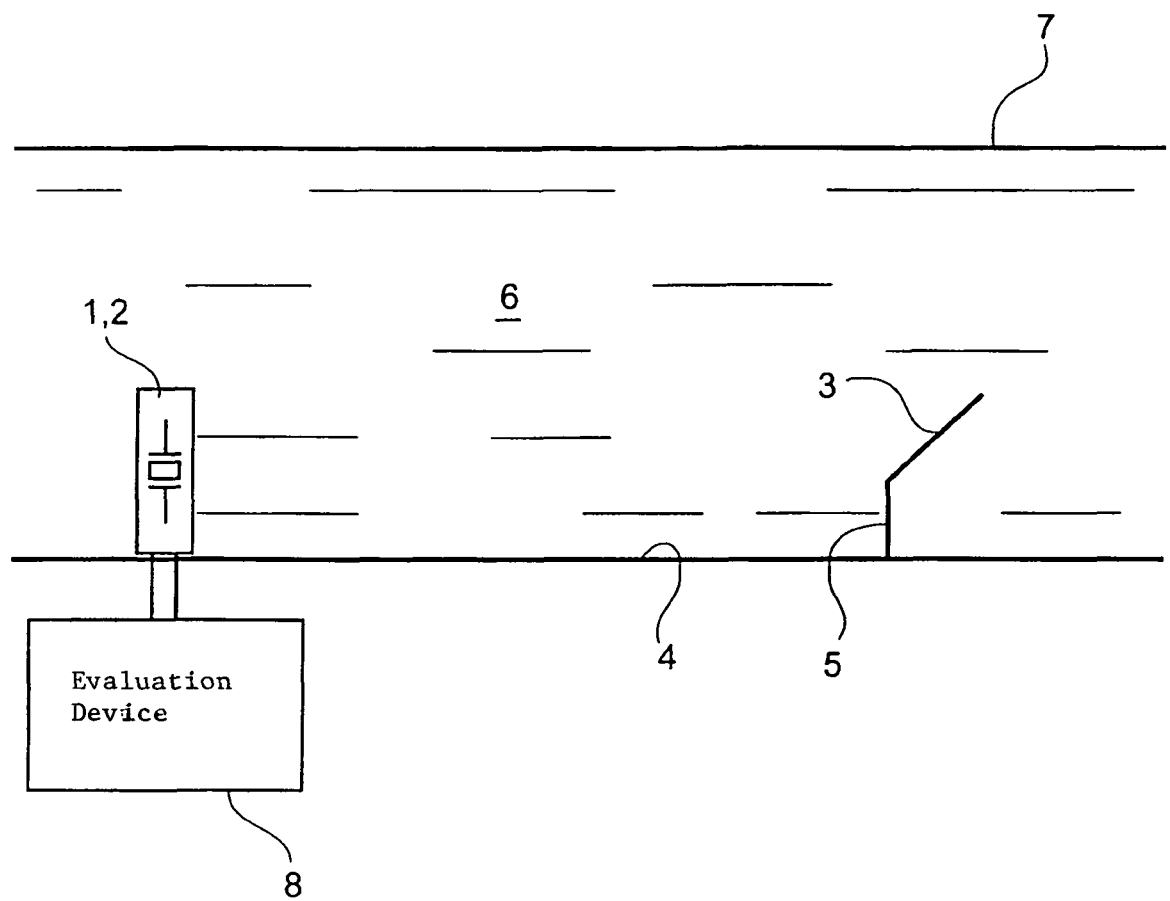
FIG. 1 is a diagrammatic view of a first embodiment of the invention within a container.

The Figures show a liquid 6 in a container. Of the container the Figures diagrammatically show a container bottom 4. Provided in the immediate proximity of the container bottom 4 is a transmitting device 1 which emits ultrasonic waves substantially parallel to the container bottom 4. Also arranged in the immediate proximity of the container bottom 4 is a receiving device 2 which receives echo signals caused by the ultrasound transmission pulses of the transmitting device 1. The transmitting device 1 and the receiving device 2 can be in the form of structural unit which has an electroacoustic transducer. The transducer can be in the form of a piezoelectric transducer device in known manner.

An evaluation device 8 is connected to the transmitting/receiving device 1, 2. The transit times of the ultrasound transmission pulses and the echo signals resulting therefrom are evaluated in known manner in the evaluation device 8 which can be in the form of an electronic computer device, to determine the filling level of the liquid 6 in the container.

A reflector 3 is also arranged in the immediate proximity of the container bottom 4. The reflector 3 can be formed by a metal or plastic surface. The metal surface can be formed by a metal portion or a metalization applied to a substrate. The reflector 3 is of such a design that it deflects the ultrasound transmission pulses emitted by the transmitting device 1 in the direction towards the surface 7 of the liquid. For that purpose the reflector 3 or the reflecting surface is at an angle of about 45° relative to the container bottom 4 or the direction of propagation of the ultrasound transmission pulses. When a horizontal arrangement is involved, the substantially horizontally emitted ultrasound transmission pulses are deflected in a vertical direction towards the surface 7 of the liquid. The deflection angle is about 90°. The deflection angle can also differ therefrom. The echo signals which are reflected by the surface 7 of the liquid and which are caused by the ultrasound transmission pulses pass back to the reflecting surface of the reflector 3 and from there are directed onto the receiving device 2 where they are received. In this case the echo signals are also diverted through about 90°. As already explained, the filling level of the liquid 6 in the container is determined from the transit times of the ultrasound transmission pulses and the related echo signals, by means of the evaluation device 8 which is connected to the transmitting/receiving device 1, 2.

For that purpose, the reflector 3 is at a given spacing relative to the transmitting/receiving device 1, 2.

Figure 2:
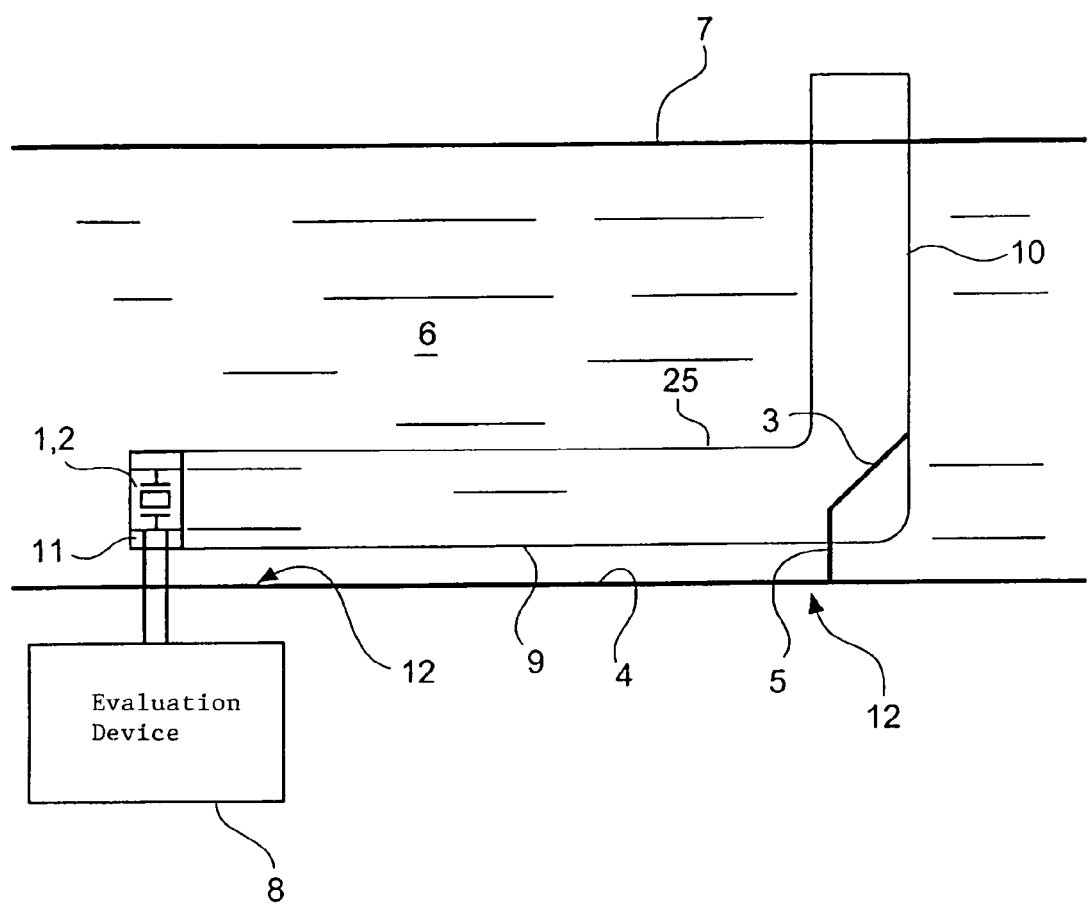
FIG. 2 is a diagrammatic view of a second embodiment of the invention within a container.

Furthermore, the illustrated embodiments of FIGS. 1 and 2 have a reference surface 5 which, like the reflector, can also comprise metal or plastic material and which is preferably in one piece with the reflector 3. The reference surface 5 is also at a predetermined spacing relative to the transmitting/receiving device 1, 2. At the reference surface 5 the ultrasound transmission pulses emitted by the transmitting device 1 substantially parallel to the container bottom 4 are reflected back in the opposite direction to the receiving device 2. By virtue of the predetermined spacing between the transmitting/receiving device 1, 2 and the reference surface 5, changes in the speed of propagation of the ultrasonic waves in the liquid 6, which result from physical changes in the liquid, can be detected and taken into consideration when determining the filling level of the liquid 6 in the container, in the context of evaluation in the evaluation device 8. In that way, when determining the filling level of the liquid, compensation is provided in respect of differences in density and temperature fluctuations and other physical properties which have an effect on the speed of propagation of the ultrasonic waves in the liquid 6. The reference surface 5 is preferably in the form of a flat surface and extends perpendicularly to the container bottom 4 or to the direction of propagation of the ultrasound transmission pulses.

Figure 3:
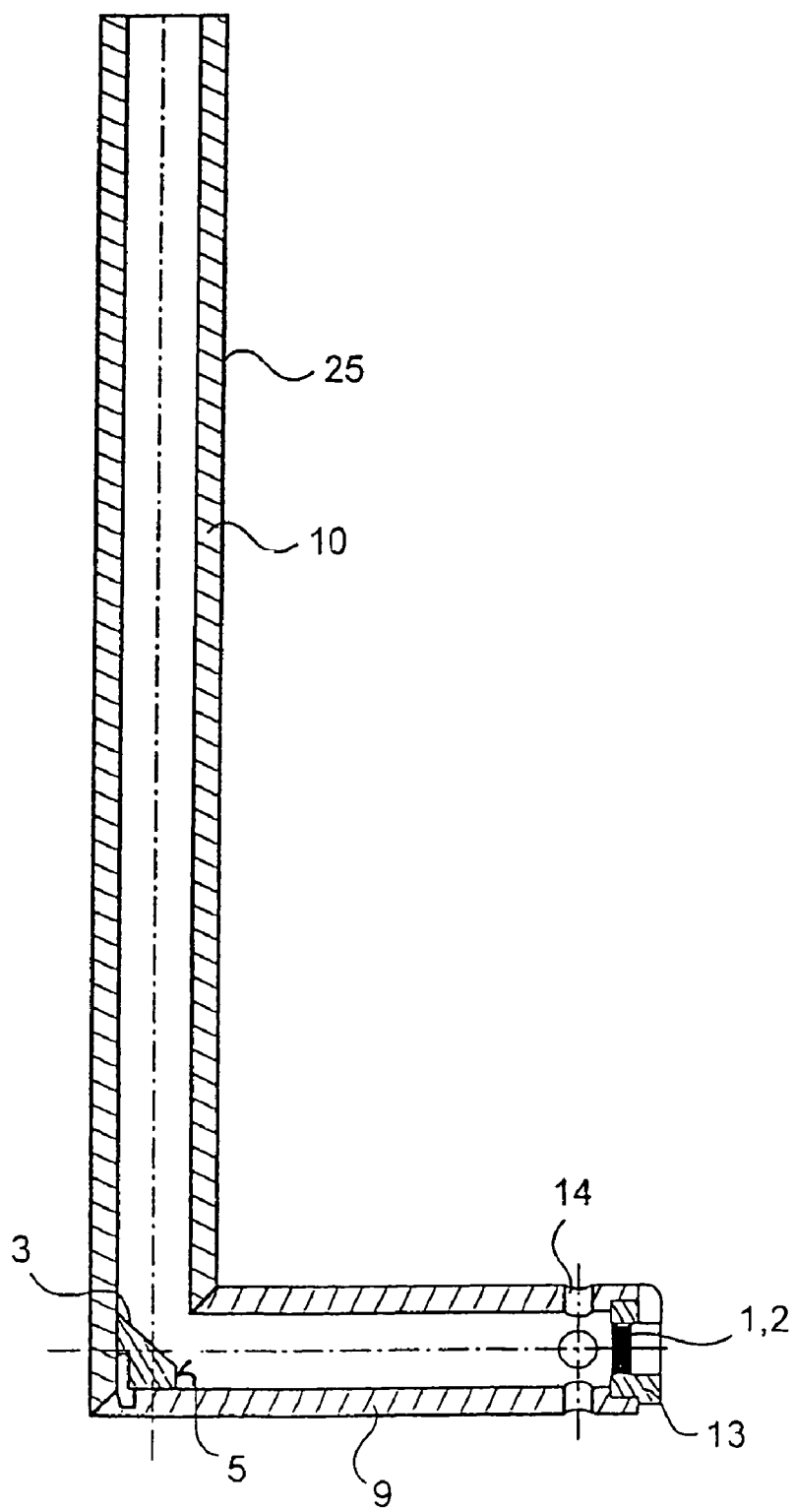
FIG. 3 is a cross-sectional view of a third embodiment.
Figure 4:
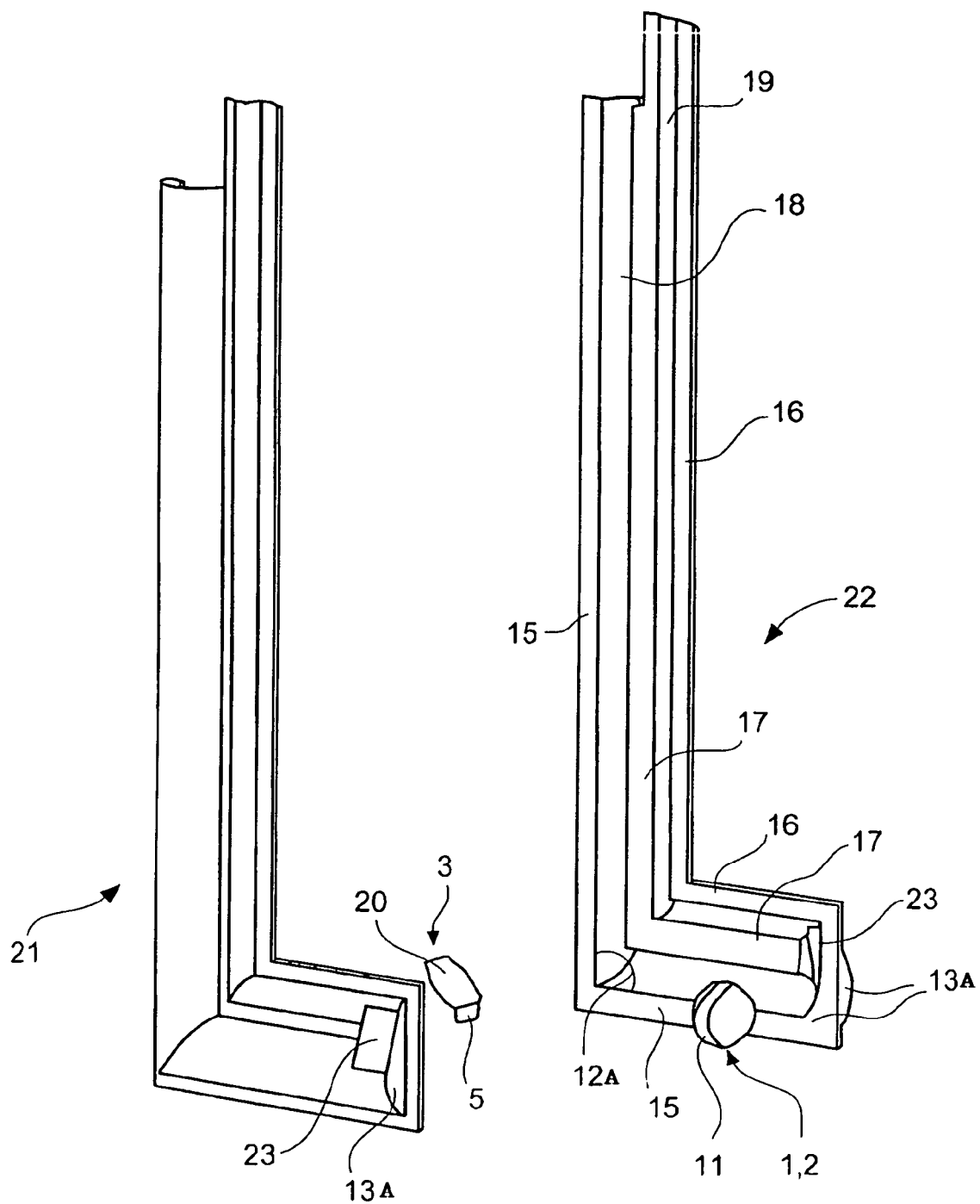
FIG. 4 is an exploded perspective view of two housing shell portions and installation fitments for a further embodiment of the invention.

In the second embodiment shown in FIG. 2, the transmitting/receiving device 1, 2, the reflector 3 and the reference surface 5 are arranged in a tube 9 extending substantially parallel to the container bottom 4. The transmitting/receiving device 1, 2 is at an end of the tube 9, that is open around the axis of the tube 9, and is held at a spacing from the inside wall of the tube by liquid-permeable spacers 11. In that way, it is possible for liquid to pass into the interior of the tube 9. The tube 9 can however have openings 14 in its tube wall, as shown in FIG. 3, so that liquid passes into the interior of the tube 9. The reflector 3 and the reference surface 5 which can consist of one piece are arranged at the other end of the tube 9. The tube 9 is opened by way of the reference surface 5 in a direction towards the surface 7 of the liquid. In the illustrated embodiments in FIGS. 2 and 3, a further tube 10 is arranged around the opening in the tube 9. Preferably the tube 10 is integrally connected to the tube 9 to form an angled tube. The level of liquid in the tube 10 corresponds to the level of liquid in the container. The embodiments of FIGS. 2 and 3, for improved measurement of the filling level, provide for calming the liquid which is in the tubes 9 and 10. The reflector 3 and the reference surface 5 are arranged in the angled region of the two tubes 9 and 10. Fixing of the tube 9 can be effected by way of fixing means 12 which, as shown in FIG. 2, provide a connection between the container bottom 4 and the tube 9 at given locations. It is however also possible to use a fixing layer between the tube 9 and the container bottom 4. The spacing between the tube 9 and the container bottom 4 is made as small as possible in order to be able to detect even low filling levels of liquid in the container. The length of the tube 10 is of a dimension depending on the liquid levels to be detected in the container and can be substantially greater than the length of the tube 9, as shown in FIG. 3.

The transmitting/receiving device 1, 2 can be held at a spacing from the inside wall of the tube at the open end of the tube 9 by means of spacers 11 so that liquid 6 can also pass into the interior of the tube. In the embodiment of FIG. 3, the transmitting/receiving device 1, 2 is held by an annular holder 13 at the end of the tube and the openings 14 are provided therebehind in the tube 9. The tubes 9, 10 are adapted to conduct ultrasound.

Figures 5, 6:
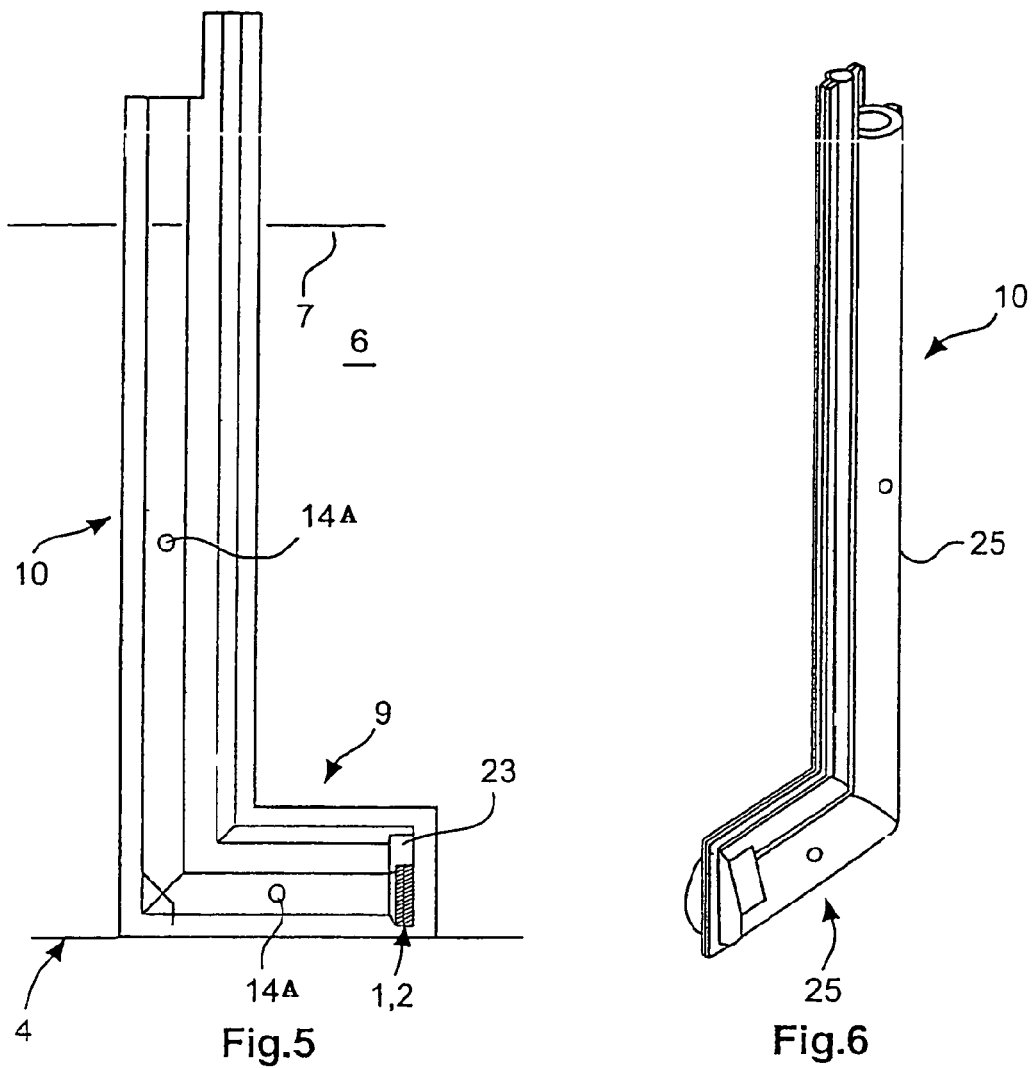
FIG. 5 is a cross-sectional view of the embodiment of FIG. 4 shown within a container.
FIG. 6 is a perspective view of the housing of the embodiment of FIG. 4.
Figure 7:
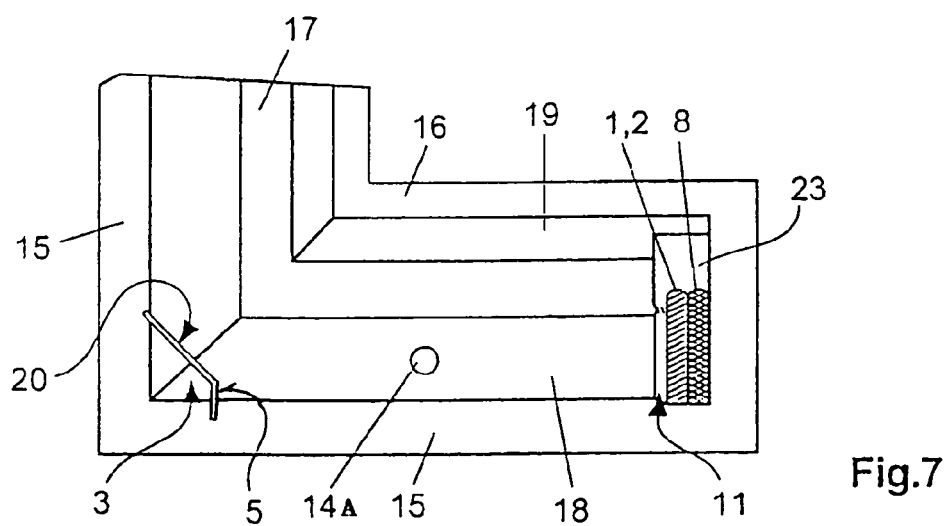
FIG. 7 is a cross-sectional view on a larger scale of the lower housing portion of the embodiment of FIG. 4 with reflector and transmitting/receiving device therein.

FIG. 5 shows a liquid 6 disposed in a container. Of the container the Figure diagrammatically shows a container bottom 4. Provided in the immediate proximity of the container bottom 4 is a transmitting device 1 which emits ultrasonic waves substantially parallel to the container bottom 4. In addition, arranged in the immediate proximity of the container bottom 4 is a receiving device 2 which receives echo signals caused by the ultrasound transmission pulses of the transmitting device 1. The transmitting device 1 and the receiving device 2 can be in the form of a structural unit having an electroacoustic transducer. In known manner that transducer can be in the form of a piezoelectric transducer device. The transducer device is supported in relation to a housing wall by means of a damping/spring element 8 (see FIG. 7).

As can be seen from FIGS. 4 through 7, the angled tubular housing 25 can comprise two half-shell portions 21 and 22. The respective tube halves are formed in those half-shell portions 21 and 22. In the illustrated embodiment, angled hollow spaces 18 and 19 are formed in the tubular housing 25. It is however also possible for the configuration of the tubular housing 25 to be such that only the angled hollow space 18 is formed, as described above, with the transmitting/receiving device 1, 2 and the reflector 3 disposed therein. The ultrasonic waves to be used for the measurement procedure are substantially guided in the angled hollow space 18, as described hereinbefore.

In the illustrated embodiment, formed in the two angled housing portions formed by the two tubes 9, 10 is an additional, correspondingly angled hollow space 19 which serves as a cable duct for electric lines which form the electrical connection between the transmitting/receiving device 1, 2 and the evaluation device (not shown) which can be disposed outside the container.

The two half-shell portions 21 and 22 are connected together sealingly, in particular in liquid-tight relationship, at connecting surfaces 15, 16 and 17. Preferably the connection is made by welding, in particular laser welding. The connecting surfaces 15, 16 and 17 are also of a configuration adapted to the angled tubular shape of the housing 25. Liquid-tight separation between the two angled hollow spaces 18 and 19 is achieved by the connecting surfaces 17 on the half-shell portions 21 and 22, which are between the two respective connecting surfaces 15 and 16, after the half-shell portions are assembled.

Openings 12A are provided at the half-shell portions 21, 22 in the hollow space 18 in the angled region at the inside surfaces which enclose the hollow space 18. Those openings 12A ensure pre-assembly of the reflector 3 before the two half-shell portions 21 and 22 are assembled. In addition, provided at the other end of the one tube 9 of the housing 25, in the two half-shell portions 21, 22, are openings 13A which permit pre-assembly of the transmitting/receiving device 1, 2. The openings 13A are of such a configuration that the damping/spring element 8, the piezoelectric transducer of the transmitting/receiving device 1, 2 and a peripherally extending seal 11 which seals off that arrangement with respect to the hollow space 18 in liquid-tight relationship can be arranged. After assembly of the two half-shell portions 21 and 22 that arrangement is positioned in a secure position with respect to the reflector 3. The openings 12A,13A provided in the interior of the housing not only permit pre-assembly of the above-mentioned components on the half-shell portions 21 and 22, but, after assembly thereof, that also ensures that the reflector 3 and the surfaces provided thereon, in particular the reflecting deflecting surface 20 and the reference surface 5 assume the prescribed position in relation to the piezoelectric transducer in the transmitting/receiving device 1, 2.

The reflector 3 with the deflecting reflecting surface 20 and the reference surface 5 is made in one piece, in particular from a flat angled portion. It can be in the form of metal sheet and can be held in the correct position in positively locking relationship in suitable slots at the inside wall of the hollow space 18 of the angled housing 25. The deflecting reflecting surface 20 and the reference surface are disposed on angled parts of the reflector which is in the form of a flat angled portion, and extend at an angle of 225° relative to each other.

Space is provided in additional openings 23 at the insides of the two half-shell portions 21 and 22 for an electrical connecting arrangement with which the electric lines which are guided in the hollow space 19 can be connected to the transmitting/receiving device 1, 2. This involves power supply lines and lines carrying a measurement signal. The hollow space 18 is additionally sealed off in liquid-tight relationship with respect to the opening 23 and the hollow space 19 by the annular seal 11.

The electric lines can be laid in the hollow space 19 prior to assembly of the two half-shell portions 21 and 22 and can be connected in the respective opening 23 of the half-shell portion to the electrical transmitting/receiving device 1, 2, in particular the piezoelectric transducer, prior to the assembly operation. As explained hereinbefore that affords easier assembly of the entire measuring apparatus.

Openings 14A in the hollow space 18 which can be provided in both tubes 9 and 10 of the housing 25 provide that liquid 6 is present in the hollow space 18. As can be seen in particular from FIG. 7 the electrical transducer of the transmitting/receiving device 1, 2 is supported by means of the damping/spring element 8 in relation to the closing housing wall of the one tube 9. That provides for satisfactory generation of the required sound wave transmission pulses and also satisfactory reception of the echo signals or the reference signals coming from the reference surface 9.

The container referred to in the specific embodiments can be a mobile tank for example arranged in a vehicle, in which fuel for an internal combustion engine or another liquid, in particular urea, is contained. It will be appreciated that the container can also be a stationary liquid container or tank.

LIST OF REFERENCE NUMERALS 1 transmitting device
2 receiving device 3 reflector
4 container bottom
5 reference surface
6 liquid
7 surface of the liquid
8 damping/spring element
9 tube
10 tube
11 seal
12 fixing means
12A openings for reflector
13 openings for transmitting/receiving device
13A openings
14 openings
14A openings
15 connecting surface
16 connecting surface
17 connecting surface
18 hollow space
19 hollow space (cable duct)
20 deflecting reflecting surface
21 half-shell portion
22 half-shell portion
23 opening for cable connection
25 housing

What is claimed is:

1. Apparatus for measuring the filling level of a liquid having a surface in a container comprising:
   a first tube extending substantially parallel to a bottom of the container and having an opening in a direction towards the surface of the liquid;
   a second tube arranged at an angle to the first tube and fixedly connected thereto at the opening of the first tube, wherein the tubes form a tubular housing comprising two half-shell portions involving the respective longitudinal extent of the tubes, the two half-shell portions are fixedly connected together at longitudinally extending connecting surfaces, the tubular housing forms two parallel hollow spaces extending in the longitudinal extent of the housing, one of the hollow spaces serves substantially for conducting ultrasound and the other hollow space serves for guiding electric lines;
   a transmitting device arranged in the first tube in proximity to the container bottom for emitting ultrasound transmission pulses;
   a receiving device arranged in the first tube in proximity to the container bottom for receiving echo signals reflected at the surface of the liquid;
   an evaluation device for evaluating transit times of the ultrasound transmission pulses and echo signals;
   a reflector arranged in the first tube in proximity to the container bottom and in the region of the opening at given spacing relative to the transmitting and receiving devices for reflecting the ultrasound transmission pulses in the direction of the surface of the liquid and in the direction of the receiving device, whereby, the direction of the ultrasound transmission pulses emitted to the reflector and the direction of the echo signals reflected by the reflector extend substantially parallel to the container bottom; and
   a reference surface arranged in the proximity of the container bottom at a given spacing relative to the transmitting and receiving devices for reflecting the ultrasound transmission pulses in a direction in opposite relationship to the direction of incidence.

2. Apparatus as set forth in claim 1, wherein the reflector is at an angle of about 45° relative to the container bottom.

3. Apparatus as set forth in claim 1, wherein that the reference surface is arranged in the immediate proximity of the reflector.

4. Apparatus as set forth in claim 1, wherein the reflector and the reference surface are formed from one piece.

5. Apparatus as set forth in claim 1, wherein the reflector and the reference surface are formed on a flat angled portion.

6. Apparatus as set forth in claim 1, wherein the reflector and the reference surface are of approximately equal width.

7. Apparatus as set forth in claim 1, wherein the reflector has a metal surface.

8. Apparatus as set forth in claim 1, wherein the reference surface is formed by a metal face.

9. Apparatus as set forth in claim 1, wherein the angle between the two tubes is approximately a right angle.

10. Apparatus as set forth in claim 1, wherein the tubes comprise plastic material.

11. Apparatus as set forth in claim 1, wherein the reflector and the reference surface are arranged in the region of the angle configuration of the two tubes.

12. Apparatus as set forth in claim 1, wherein the transmitting and receiving devices are arranged at an open end of the first tube.

13. Apparatus as set forth in claim 1, wherein the echo signals of the reference surface are evaluated to determine the nature of the liquid.

14. Apparatus as set forth in claim 1, wherein the tubes are adapted to be ultrasound conducting.

15. Apparatus as set forth in claim 1, wherein the two half-shell portions are two angled half-shell portions.

16. Apparatus as set forth in claim 1, wherein the housing is in the form of an angled housing and the reflector is arranged in the angled housing portion.

17. Apparatus as set forth in claim 16, wherein the housing is angled through 90°.

18. Apparatus as set forth in claim 1, wherein one of the tubes of the housing is to be arranged substantially parallel to the container bottom and the other tube of the housing extends substantially perpendicular thereto.

19. Apparatus as set forth in claim 1, wherein the reflector has a reflecting surface deflecting the respective direction of propagation of the ultrasound transmission pulses and echo signals at an angle of 90°.

20. Apparatus as set forth in claim 1, wherein the ultrasonic waves directed onto the reference surface and reflected back therefrom are of a direction of propagation substantially parallel to the container bottom.

21. Apparatus as set forth in claim 1, wherein the two half-shell portions are connected together at the connecting surfaces by welding.

22. Apparatus as set forth in claim 1, wherein the two half-shell portions are connected together by means of latching means which engage sealingly into each other and which extend longitudinally at the connecting surfaces.

23. Apparatus as set forth in claim 1, wherein the reflector and the reference surface are held in the housing in positively locking relationship at an inside wall of the hollow space.

* * * * *

UNITED STATES PATENT AND TRADEMARK OFFICE
CERTIFICATE OF CORRECTION

PATENT NO. : 8,037,752 B2  
APPLICATION NO. : 12/226179  
DATED : October 18, 2011  
INVENTOR(S) : Wilfried Zachmann et al.

Page 1 of 1

It is certified that error appears in the above-identified patent and that said Letters Patent is hereby corrected as shown below:

1. On the cover page of the patent, please add the following references: Under US Patent Documents, please add --5,471,872, 12/1995, Cummings-- and --2005/0284217 A1, 12/2005, Miyagawa et al.--. Under Foreign Patent Documents, please add --JP, 2004340911 A, 12/2004, JP, 2004286528 A, 10/2004, DE, 10312100 A1, 9/2004, DE, 19932344 A1, 1/2001-- and --WO 91/02950 A, 3/1991--.

Signed and Sealed this  
Fifth Day of February, 2013

Teresa Stanek Rea  
*Acting Director of the United States Patent and Trademark Office*